(12) United States Patent
Arba Mosquera

(10) Patent No.: US 11,730,626 B2
(45) Date of Patent: Aug. 22, 2023

(54) METHOD FOR PROVIDING CONTROL DATA FOR AN EYE SURGICAL LASER OF A TREATMENT APPARATUS, CONTROL DEVICE AND TREATMENT APPARATUS

(71) Applicant: SCHWIND eye-tech-solutions GmbH, Kleinostheim (DE)

(72) Inventor: Samuel Arba Mosquera, Aschaffenburg (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 0 days.

(21) Appl. No.: 17/514,508

(22) Filed: Oct. 29, 2021

(65) Prior Publication Data

US 2022/0133540 A1 May 5, 2022

(30) Foreign Application Priority Data

Oct. 30, 2020 (DE) ...................... 10 2020 128 625.2

(51) Int. Cl.
*A61F 9/008* (2006.01)

(52) U.S. Cl.
CPC ...... *A61F 9/00827* (2013.01); *A61F 9/00804* (2013.01); *A61F 2009/00848* (2013.01)

(58) Field of Classification Search
CPC .............. A61F 9/00827; A61F 9/00804; A61F 2009/00848
See application file for complete search history.

(56) References Cited

U.S. PATENT DOCUMENTS

| | | | | |
|---|---|---|---|---|
| 2011/0082542 A1* | 4/2011 | Norrby | ................. | A61B 3/1035 351/159.73 |
| 2012/0035598 A1* | 2/2012 | Stobrawa | ................. | A61F 9/008 606/5 |
| 2016/0161764 A1* | 6/2016 | Bakaraju | ................. | A61F 2/1616 351/159.01 |
| 2017/0000336 A1* | 1/2017 | Ensing | ................. | A61B 3/1035 |

* cited by examiner

*Primary Examiner* — Brian T Gedeon
*Assistant Examiner* — Joshua Andrew Schum-Houck
(74) *Attorney, Agent, or Firm* — Medler Ferro Woodhouse & Mills PLLC

(57) ABSTRACT

A method is disclosed for providing control data for an eye surgical laser of a treatment apparatus for the removal of a tissue. The method includes using a control device for determining a wavefront of a cornea and Zernike polynomials from the wavefront and calculating a respective tissue geometry for each Zernike polynomial. A combination of Zernike polynomials describes a tissue removal geometry. The control device ascertains a subgroup of the Zernike polynomials by an optimization calculation, which uses a preset condition to select Zernike polynomials. The condition is preset by a maximized target corneal geometry and a target imaging correction to be achieved. The target corneal geometry is a difference between a corneal geometry and the tissue removal geometry. An optimized tissue removal geometry is found using the subgroup and control data for controlling the eye surgical laser, which uses the optimized tissue removal geometry for separating the tissue.

20 Claims, 3 Drawing Sheets

METHOD FOR PROVIDING CONTROL DATA FOR AN EYE SURGICAL LASER OF A TREATMENT APPARATUS, CONTROL DEVICE AND TREATMENT APPARATUS

The present invention relates to a method for providing control data for an eye surgical laser of a treatment apparatus for the removal of tissue. In addition, the invention relates to a treatment apparatus with at least one eye surgical laser and at least one control device for performing the method, to a computer program and to a computer-readable medium.

Treatment apparatuses and methods for controlling ophthalmological lasers for correcting an optical visual disorder and/or pathologically or unnaturally altered areas of the cornea are known in the prior art. Therein, pulsed lasers and a beam focusing device can for example be formed such that laser pulses effect a photodisruption and/or photoablation in a focus located within the organic tissue to remove a tissue, in particular a tissue lenticule, from the cornea. Therein, the treatments for compensating for optical visual disorders become more and more accurate. For example, a plurality of refractive errors as well as for example myopia, hyperopia and astigmatism can be corrected by means of the Lasik (laser in situ keratomileusis) method.

A disadvantage of the previous Lasik methods was the generation of spherical aberrations such as for example halos and a reduced contrast sensitivity. In order to avoid these aberrations and also to correct existing aberrations of the eye, it is known to include wavefront measurements of the eye in planning the treatment. In particular, a wavefront from a wavefront analysis can be decomposed into Zernike polynomials of multiple orders, wherein each of the Zernike polynomials can describe a refraction or aberration effect of the eye. In other words, Zernike polynomials can be used to represent wavefronts, which in turn describe imaging errors of optical systems.

In today's treatment methods, it is problematic that it is attempted to correct the imaging errors on the one hand, but partially more tissue is removed hereto than required for the correction on the other hand. Therein, it is disadvantageous that tissue of the eye once removed can no longer or only very difficultly be recovered afterwards, which can have a disadvantageous impact on a patient.

The invention is based on the object to provide control data for controlling an eye surgical laser for correcting a visual disorder, in which the tissue of the resulting target cornea can be maximized.

This object is solved by the method according to the invention, the apparatuses according to the invention, the computer program according to the invention as well as the computer-readable medium according to the invention. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

A first aspect of the invention relates to a method for providing control data for an eye surgical laser of a treatment apparatus for the removal of tissue, wherein the method comprises the following steps performed by a control device. Therein, an appliance, an appliance component or an appliance group is understood by a control device, which is configured for receiving and evaluating signals as well as for providing, for example generating, control data. For example, the control device can be configured as a control chip, computer program, computer program product or control unit. Ascertaining a wavefront of a cornea of a human or animal eye from predetermined examination data, ascertaining Zernike polynomials from the ascertained wavefront, wherein the Zernike polynomials describe imaging errors, and calculating a respective tissue geometry for each Zernike polynomial are effected by the control device, wherein an alteration of the cornea for correcting the imaging errors is specified by the respective tissue geometry and wherein a combination of a selection of the Zernike polynomials describes a tissue removal geometry. In other words, a wavefront of a cornea of the eye is first determined from previously determined examination data. For example, the examination data can be effected by retrieving the examination data from a data storage or data server or the examination data can for example be measured by means of the treatment apparatus. For example, the wavefront can be determined from an aberrometry, which can also be referred to as wavefront analysis and which can for example be performed with a Hartmann-Shack sensor. This wavefront can be decomposed into Zernike polynomials by means of known methods, wherein a respective Zernike polynomial can describe an imaging error or a portion of an imaging error. Subsequently, a respective tissue removal geometry can be determined for each Zernike polynomial by means of known methods, in particular by means of the concept of equivalent defocusing, wherein the equivalent defocusing is defined as the amount of the defocus, which is required to generate the same wavefront variance, which can be found in one or more higher order aberrations. In particular, a dioptric equivalent can be calculated, which each Zernike polynomial has. Therein, a combination of one or more Zernike polynomials can describe a tissue removal geometry, which specifies a geometry of the tissue, which can be removed for correcting the imaging errors.

Further, ascertaining a subgroup of the ascertained Zernike polynomials by an optimization calculation, by which one or more Zernike polynomials are selected for the subgroup if they satisfy a preset optimization condition, is effected by the control device, wherein the optimization condition is preset by a maximized target corneal geometry and an imaging correction to be achieved, wherein the target corneal geometry is ascertained from a difference of a corneal geometry and the tissue removal geometry. Further, ascertaining an optimized tissue removal geometry of the tissue to be removed by means of the ascertained subgroup of the Zernike polynomials is effected by the control device, wherein the optimized tissue removal geometry is determined by means of a combination of the tissue geometries of the Zernike polynomials of the subgroup. Finally, control data for controlling the eye surgical laser, which uses the optimized tissue removal geometry for separating the tissue, can be provided by the control device. In other words, one or more Zernike polynomials can be associated with a subgroup by an optimization calculation if the corresponding Zernike polynomials satisfy a preset optimization condition. The optimization condition can include that an imaging correction to be achieved is achieved, that is the visual disorder is corrected, and that a target corneal geometry as the geometry, which the cornea is to have after the treatment, is maximized. One obtains a maximized target corneal geometry in that it is iteratively examined by the optimization calculation, by which combination of the Zernike polynomials the imaging correction planned by the treatment is achieved and a maximum tissue remains for the cornea at the same time, wherein those Zernike polynomials, for which this is the case, are associated with the subgroup. Herein, it can always be paid attention to the fact how the postoperative cornea, thus the target corneal geometry, is to look like. If one has ascertained the corresponding Zernike polynomials and associated them with the subgroup, which achieve a maximum target corneal geometry, an optimized tissue removal geometry for removing the tissue can be determined from the Zernike polynomial of the subgroup by combination of the tissue geometries of the Zernike polynomials of the subgroup and the optimized tissue removal geometry can be provided to the eye surgical laser by control data for separating the tissue.

By the invention, the advantage arises that a safety in the treatment with the treatment apparatus can be further increased and a degree of the improvement for high-grade irregular corneas can also be improved since it is no longer only paid attention to the tissue to be removed, but it is paid attention to the target corneal geometry. Overall, the tissue to be removed can be minimized and the cornea after the treatment can be maximized by the method, which can be gentler for the patient.

The invention also includes forms of configuration, by which additional advantages arise.

According to an advantageous form of configuration, it is provided that a refractive correction to be achieved is preset by the imaging correction of the optimization condition, wherein those Zernike polynomials, by which the refractive correction is achieved, are fixedly associated with the subgroup, wherein the remaining Zernike polynomials, which are not fixedly associated with the subgroup, are examined for presence of the maximized target corneal geometry of the optimization condition. In particular, Zernike polynomials can describe a refractive correction and an aberration correction as the imaging correction. In this form of configuration, it is provided that the Zernike polynomials, which are preset for the refractive correction, are fixedly associated with the subgroup, thus are not influenced by the optimization calculation. However, all of the further Zernike polynomials, which are not responsible for the refractive correction, can be examined for presence of the optimization condition by optimization calculation to obtain a maximized target corneal geometry. Preferably, it is provided for the refractive correction that Zernike polynomials up to second order are preset. This means that Zernike polynomials of the zeroth, first and second order, which describe the refractive correction, are fixedly associated with the subgroup. By this form of configuration, the advantage arises that a refraction can be safely corrected in the treatment of the eye and the target corneal geometry can be maximized by the remaining Zernike polynomials at the same time.

In a further advantageous form of configuration, it is provided that an aberration correction to be achieved is preset by the imaging correction of the optimization condition, wherein those Zernike polynomials, by which the aberration correction is achieved, are fixedly associated with the subgroup, wherein the remaining Zernike polynomials, which are not fixedly associated with the subgroup, are examined for presence of the maximized target corneal geometry of the optimization condition. This means that the aberration correction to be achieved is fixedly preset in this form of configuration in that the responsible Zernike polynomials are associated with the subgroup, wherein the Zernike polynomials responsible for the refractive correction can thus be examined for presence of the maximized target corneal geometry. Preferably, it is provided that Zernike polynomials from the third order are preset for the aberration correction.

It is advantageous that the optimization condition is preset by a resulting geometry and/or morphology and/or thickness of the target corneal geometry. In other words, it can be taken into account, which morphology a patient eye has, and the optimization condition of the target corneal geometry can be adapted thereupon. A geometry and thickness, respectively, of the cornea can also be taken into account and preset such that it can be paid attention to the fact at which location of the cornea more tissue is available for removal and at which location less is available. Thus, the target corneal geometry can be individually adapted for each patient, whereby a safety and a treatment result can be improved.

According to a further advantageous form of configuration, it is provided that the optimization condition is satisfied if a thickness or a volume of the target corneal geometry is maximized. This means that either a thickness of the cornea in the direction of an optical axis of the eye can be maximized or the total volume of the cornea for determining the target corneal geometry is to be maximized. Thus, a parameter for the optimization condition can be provided in advantageous manner, which is to be iteratively improved.

According to a further advantageous form of configuration, it is provided that the Zernike polynomials are associated with the subgroup with a factor determined by the optimization calculation, wherein a value between 0 and 1 is calculated for the factor. In other words, it is provided that the Zernike polynomials are associated with the subgroup not only completely or not at all, but also with a proportion assigned by the factor. This means that Zernike polynomials can for example have only a 50 percent proportion of the original value and thus are not completely ascribed to the tissue removal geometry. Preferably, it is provided that the factor can also adopt the values of 0 and 1, this means that a respective Zernike polynomial with factor of 0 is not associated with the subgroup and a Zernike polynomial with factor of 1 is completely associated with the subgroup. In particular, the factor can be every real number between 0 and 1 and thus specify the proportion of the Zernike polynomial in the subgroup. Hereby, the advantage arises that the target corneal geometry and the imaging correction to be achieved can be even more accurately determined.

According to a further advantageous form of configuration, it is provided that a refractive power value, in particular a dioptric equivalent value, is determined for respective ranges of the respective Zernike polynomials, wherein an association of the one or the multiple Zernike polynomials with the subclass is performed depending on at least one preset refractive power value range. In other words, ranges of the Zernike polynomials have refractive power values, which can in particular be present as dioptric equivalent values. This means that each range of a respective Zernike polynomial stands for one refractive power value, wherein the refractive power value can preferably be obtained by means of a calculation from a dioptric equivalent value. In particular, the Zernike polynomials can be represented with a part depending on radius and a part depending on angle, for example like a wavefront map with height lines, wherein the respective height can specify the refractive power value. A dioptric equivalent value is an optical blur of the individual Zernike polynomial, which can be calculated in the unit diopter. In this form of configuration, a refractive power value range can be preset as the optimization condition for the imaging correction to be achieved, wherein Zernike polynomials having refractive power values in this refractive power value range can be fixedly associated with the subgroup. Herein, the association of the Zernike polynomials with the subclass depending on the refractive power value range represents a part of the imaging correction to be achieved, this means that the refractive power value range can be rated as a parameter of the imaging correction to be achieved, to examine the optimization condition. Preferably, the refractive power value can be present in diopters and the refractive power value range can represent a range with diopter values, which are to be fixedly corrected, for example from less than −0.5 diopters and greater than 0.5 diopters. In particular, the refractive power value range can have high diopter values, by which a high proportion can be taken into account for correcting the visual disorder. Particularly preferably, the respective Zernike polynomial, which is associated with the subclass, can only be associated with the subclass with the respective range, which has the refractive power value in the preset refractive power value range. Thus, other ranges/proportions of the Zernike polynomials can remain unconsidered and/or the other ranges can be separately optimized.

It is advantageous if an own refractive power value range is preset for each Zernike polynomial and/or for each order of the Zernike polynomials. Thus, a higher individualization can be achieved, and different Zernike polynomials can be differently weighted in considering the refractive power values.

According to a further advantageous form of configuration, it is provided that value range classes with respective refractive power value ranges are preset, wherein the respective ranges of the respective Zernike polynomials are classified into the preset value range classes depending on the refractive power value, wherein it is classified by the value range classes how important the respective range is for the imaging correction to be achieved, wherein the association of the one or multiple Zernike polynomials with the subclass is performed depending on the value range classes. This means that ranges of the respective Zernike polynomials can have refractive power values, which can be classified into value range classes. This can be performed based on preset refractive power value ranges. In particular, the value range classes can specify how important the respective range is for the imaging correction to be achieved, for example how high the refractive power value is in this range. Then, the association of the Zernike polynomials can be performed based on these value range classes, for example it can be specified that only Zernike polynomials, which have clinically relevant value ranges, are allowed to be associated with the subgroup. Hereby, one obtains a simple and fast allocation of the most important Zernike polynomials to the subclass.

Preferably, it is provided that at least one of the value range classes is selected, wherein Zernike polynomials with refractive power values outside of the selected value range class are fixedly associated with the subgroup, wherein those refractive power values, which are within the refractive power value range of the selected value range class, are additionally optimized within the refractive power value ranges of the selected value range classes for maximizing the target corneal geometry by the optimization calculation. In other words, a value range class can be selected, which is not fixedly associated with the subgroup. The refractive power values, which are in the selected value range class, can then be altered, preferably optimized, by the optimization calculation for maximizing the target corneal geometry in that the refractive power values within the selected refractive power value range can be altered. This means that the height lines of the Zernike polynomials are allowed to be altered by the optimization calculation if they are in the selected refractive power value range. Preferably, the refractive power values within the refractive power value range are altered such that one finally obtains the maximized target corneal geometry. This is to be explained based on an example below. For example, a value range class with clinically non-relevant refractive power values can be selected, for example refractive power values between −0.25 diopters and +0.25 diopters. That is, all of the Zernike polynomials, which have refractive power values above an amount of 0.25 diopters, can be fixedly associated with the subgroup. However, the Zernike polynomials of the selected value range class can be altered by the optimization calculation and a respective refractive power value within the selected value range class can be optimized between −0.25 diopters and +0.25 diopters such that a maximized target corneal geometry is finally obtained. Alternatively, multiple value range classes can also be selected, the refractive power values of which are optimized within the refractive power value range of the selected value range classes. For example, in addition to the value range class with an amount of 0.25 diopters, the value range class with an amount of up to 0.5 diopters can be selected, wherein the refractive power values of these two value range classes can then be altered within the amount of 0.5 diopters to obtain the maximized target corneal geometry.

Preferably, it is provided that at least one of the value range classes is selected, wherein the refractive power values of all of the value range classes are optimized for maximizing the target corneal geometry by the optimization calculation, wherein the refractive power values are increased or reduced by a respective optimization value for optimization, wherein the respective optimization value is within the refractive power value ranges of the selected value range classes. This means that at least one of the value range classes can first be selected, by which a refractive power value range can be preset. The refractive power values of all of the value range classes can now be increased or reduced based on the selected refractive power value range, wherein the optimization value, by which the refractive power values of all of the value range classes can be increased or reduced, has to be within the refractive power value range of the selected value range class. Below, this is to be illustrated based on an example. For example, a value range class can again be selected, which has refractive power values with an amount of up to 0.25 diopters. In another value range class, a Zernike polynomial can have a value of 0.7 diopters in a range, wherein this refractive power value is allowed to be altered by the selected 0.25 diopters in the optimization calculation. This means that the refractive power value of the Zernike polynomial is allowed to be altered between 0.45 diopters and 0.95 diopters, thus 0.7 diopters+−0.25 diopters. Correspondingly, all of the further refractive power values of each value range class can be adapted by the optimization value, which is preset by the selected value range class. Thus, all of the refractive power values can preferably be minimally optimized to obtain a maximized target corneal geometry. Preferably, the optimization value can be selected such that the imaging correction is further sufficient, but tissue can be saved.

Particularly preferably, it is provided that the ranges of the Zernike polynomials are divided into three value range classes, wherein the first value range class includes refractive power values below 0.25 diopters and is categorized as clinically non-relevant, the second value range class includes refractive power values between 0.25 diopters and 0.5 diopters and is categorized as possibly clinically relevant, and the third value range class comprises refractive power values above 0.5 diopters and is categorized as clinically relevant, wherein Zernike polynomials, which have the third value range class or have a combination of the second and the third value range class, are fixedly associated with the subgroup, wherein the remaining Zernike polynomials, which are not fixedly associated with the subgroup, are examined for presence of the maximized target corneal geometry of the optimization condition. The previously specified diopter values are to be understood as magnitude values, which means that the first value range class extends from −0.25 to 0.25 diopters, the second value range class extends from −0.5 to −0.25 and 0.25 to 0.5 diopters and the third value range class of refractive power values extends above 0.5 diopters and below −0.5 diopters. Thus, it can in particular be easily specified if only clinically relevant or clinically possibly relevant Zernike polynomials are fixedly associated and the remaining Zernike polynomials are examined for presence of the maximized target corneal geometry according to the optimization condition and are possibly not associated with the subgroup.

A second aspect of the present invention relates to a control device, which is configured to perform one of the above described methods. The above cited advantages arise. The control device can for example be configured as a control chip, control unit or application program ("app"). The control device can preferably comprise a processor device and/or a data storage. An appliance or an appliance component for electronic data processing is understood by a processor device. The processor device can for example comprise at least one microcontroller and/or at least one microprocessor. Preferably, a program code for performing the method according to the invention can be stored on the optional data storage. The program code can be configured, upon execution by the processor device, to cause the control device to perform one of the above described embodiments of one or both methods according to the invention.

A third aspect of the present invention relates to a treatment apparatus with at least one eye surgical laser for the separation of a tissue predefined by the control data, in particular of a corneal volume with predefined interfaces of a human or animal eye, by means of photodisruption and/or photoablation, and at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually introduce pulsed laser radiation with a pulse duration between 1 fs and 1 ns into the corneal tissue. Thereby, the power density of the respective laser pulse required for the optical breakthrough can be spatially narrowly limited such that a high incision accuracy is allowed in the generation of the interfaces. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data for removing the tissue determined in the method.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including commands, which cause the treatment apparatus according to the third inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims: There shows:

In the figures, identical or functionally identical elements are provided with the same reference characters.

Figure 1:
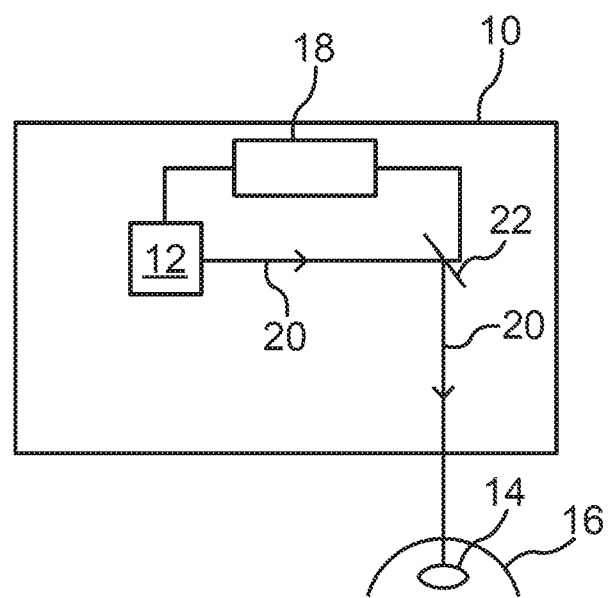
FIG. 1 is a schematic representation of a treatment apparatus according to the invention according to an exemplary embodiment.

FIG. 1 shows a schematic representation of a treatment apparatus 10 with an eye surgical laser 12 for the removal of a tissue 14 of a human or animal eye 16 by means of photodisruption and/or photoablation. For example, the tissue 14 can represent a lenticule or also volume body, which can be separated from a cornea of the eye 16 for correcting a visual disorder by the eye surgical laser 12. A geometry of the tissue 14 to be removed, thus a tissue removal geometry 14, can be provided by a control device 18, in particular in the form of control data, such that the laser 12 emits pulsed laser pulses in a pattern predefined by the control data into the cornea of the eye 16 to remove the tissue 14. Alternatively, the control device 18 can be a control device 18 external with respect to the treatment apparatus 10.

Furthermore, FIG. 1 shows that the laser beam 20 generated by the laser 12 can be deflected towards the eye 16 by means of a beam deflection device 22, namely a beam deflection device such as for example a rotation scanner, to remove the tissue 14. The beam deflection device 22 can also be controlled by the control device 18 to remove the tissue 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. In addition, the control device 18 optionally comprises a storage device (not illustrated) for at least temporary storage of at least one control dataset, wherein the control dataset or datasets include(s) control data for positioning and/or for focusing individual laser pulses in the cornea. The position data and/or focusing data of the individual laser pulses, that is the tissue removal geometry 14, is ascertained based on the method described below.

Figure 2:
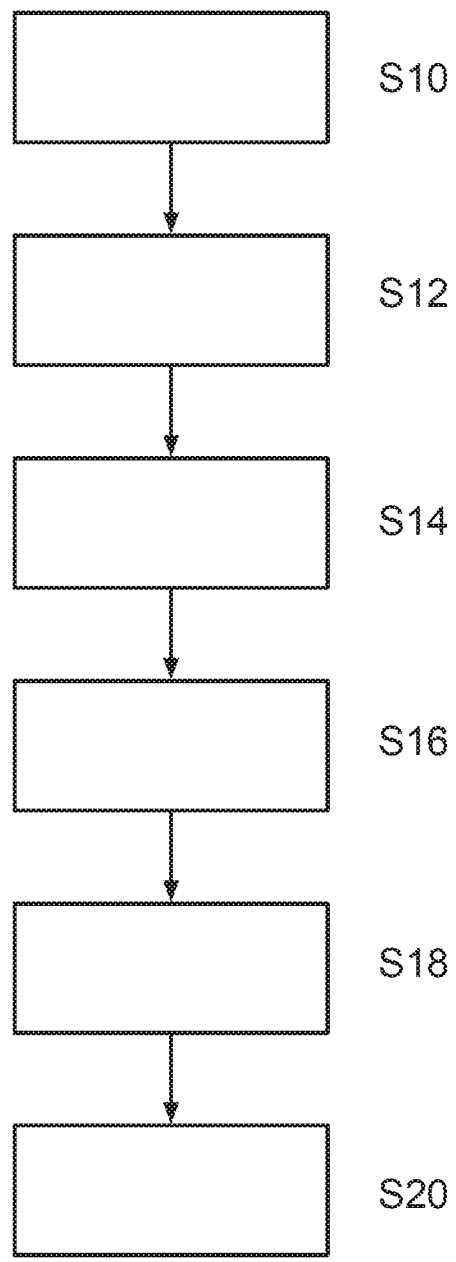
FIG. 2 is a schematic method diagram according to an exemplary embodiment.

In FIG. 2, a schematic method diagram for providing control data for the eye surgical laser 12 of the treatment apparatus 10 for the removal of the tissue 14 is illustrated. In a step S10, a wavefront of a cornea of a human or animal eye 16 is ascertained from predetermined examination data. The wavefront can for example be ascertained by means of a wavefront analysis. Subsequently, in a step S12, Zernike polynomials can be determined from the ascertained wavefront, wherein the Zernike polynomials can describe imaging errors of the eye 16. Therein, a so-called Zernike pyramid 24 is for example illustrated in FIG. 3, wherein the Zernike polynomials from zeroth order O0 up to the eighth order O8 are schematically illustrated. By means of the Zernike polynomials, a respective tissue geometry can then be calculated for each Zernike polynomial in a step S14, wherein the tissue geometry can specify an alteration of the cornea for correcting an imaging error and wherein a selection of the Zernike polynomials can describe a tissue removal geometry. That means that it is determined how the tissue looks like, which is described by one or more Zernike polynomials, which is to be removed for correcting the imaging error.

In a step S16, a subgroup of the Zernike polynomials can then preferably be iteratively ascertained, by which a maximized target corneal geometry and an imaging correction to be achieved can be provided. This means that a preset imaging correction is to be achieved on the one hand, which corrects the imaging error or errors, and the residual tissue of the cornea, that is the target corneal geometry, is to be maximized on the other hand. In order to achieve this, an optimization calculation can be performed, in which one or more Zernike polynomials are selected for the subgroup if they satisfy a preset optimization condition, wherein the optimization condition can be preset by the maximized target corneal geometry and the imaging correction to be achieved. In particular, the target corneal geometry can be determined from a difference of an original corneal geometry and the tissue removal geometry, which can be ascertained by the combination of the selection of the Zernike polynomials.

Figure 3:
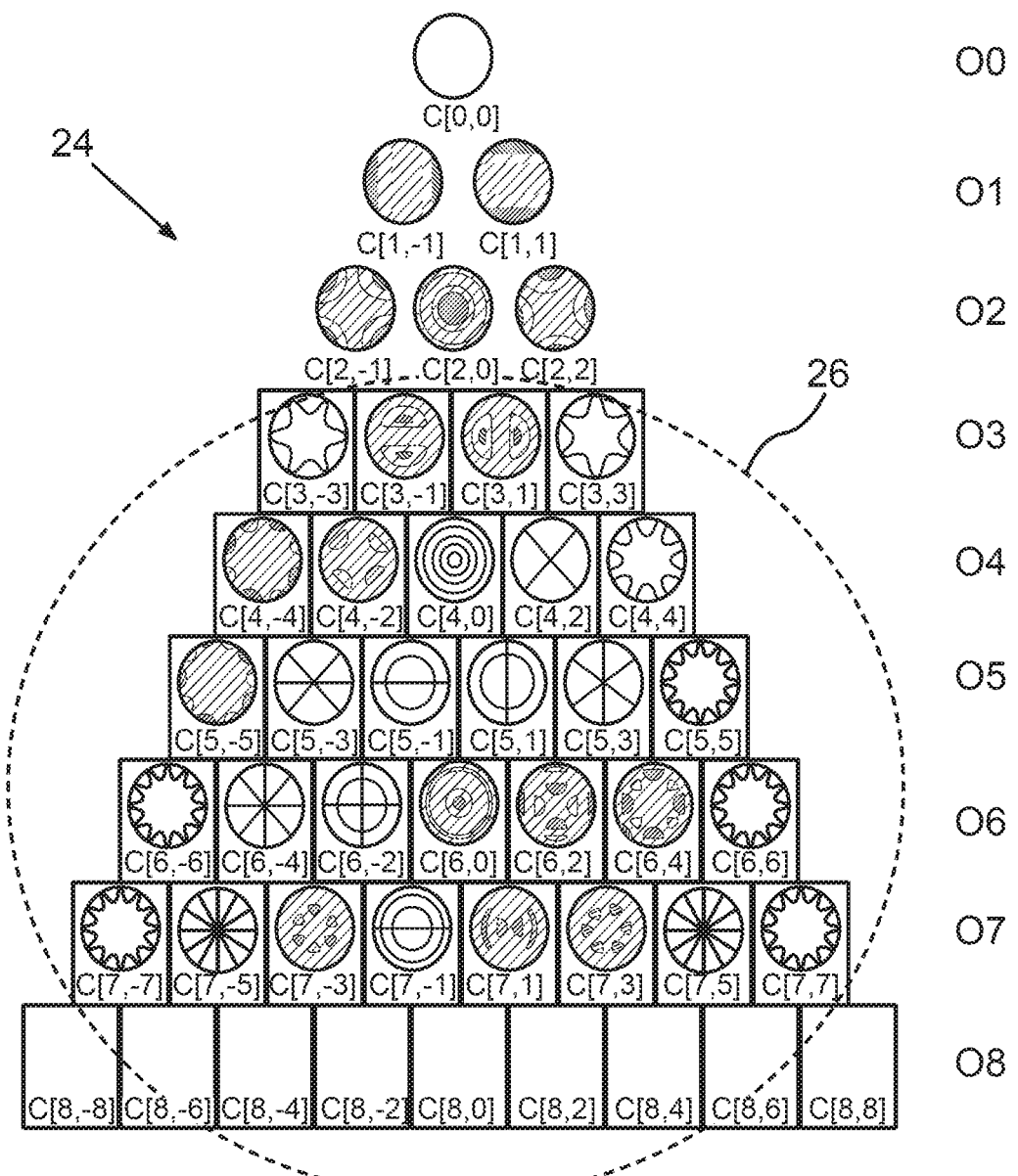
FIG. 3 is a schematic representation of a Zernike pyramid.

Step S16 is to be explained below based on the Zernike pyramid 24 illustrated in FIG. 3. As previously described, a respective Zernike polynomial with the respective order O0 to O8 is here illustrated, which have been determined from the wavefront of the cornea. From the division into the individual Zernike polynomials, it can result that not all of the Zernike polynomials have an identical correction proportion for correcting the imaging error, but only tissue is removed, which does not have a great proportion of the imaging correction, by application of some of the Zernike polynomials. In particular, it can be ascertained by the optimization calculation, which ones of the Zernike polynomials are mainly responsible for the imaging correction to be achieved and result in the maximized target corneal geometry at the same time, wherein they can be associated with the subgroup, which is for example illustrated in FIG. 3 based on the hatched Zernike polynomials.

Preferably, it can be provided that it can be preset in the imaging correction to be achieved if a refractive correction or an aberration correction is to be achieved. In the embodiment illustrated in FIG. 3, a refractive correction can for example be preset, wherein the Zernike polynomials up to the second order O2 are preset for refractive correction and are fixedly associated with the subgroup. That means that the Zernike polynomials up to the second order O2 are not taken into account by the optimization calculation, but directly belong to the subgroup. However, the Zernike polynomials 26 responsible for the aberration correction can be examined for presence of the optimization condition by the optimization calculation and thus be associated with the subgroup or not. Preferably, it can be provided that the Zernike polynomials 26 to be optimized are associated with the subgroup with a factor determined by the optimization calculation, wherein the factor can have a value between 0 and 1. In other words, a Zernike polynomial, which is associated with the subgroup with the factor of 0, can be deactivated, thus no association with the subgroup, and a Zernike polynomial, which is associated with the subgroup with the factor of 1, is completely taken into account. In addition, a Zernike polynomial of the Zernike polynomials 26 to be optimized can also be proportionally taken into account, that means that the factor can adopt an intermediate value between 0 and 1, for example 0.75, wherein the respective Zernike polynomial is then only taken into account by 75 percent and has a correspondingly lower tissue removal geometry and also a lower imaging correction.

Particularly preferably, it can be provided that refractive power values for respective ranges of the Zernike polynomials are determined, wherein the association of the Zernike polynomials with the subclass is performed depending on a preset refractive power range value. In particular, value range classes can be preset, wherein each value range class has an own refractive power value range. That means that a refractive power value, which is in a respective refractive power value range, is associated with a value range class. In particular, a first value range class can have refractive power values below 0.25 diopters, a second value range class can have refractive power values between 0.25 diopters and 0.5 diopters, and a third value range class can have refractive power values above 0.5 diopters. The first value range class can for example be categorized as clinically non-relevant and it can be preset by the optimization calculation that Zernike polynomials, which only have refractive power values of the first value range class, are not associated with the subgroup. The second value range class can for example be categorized as possibly clinically relevant and be examined for presence of the optimization condition, and the third value range class can be categorized as clinically relevant, wherein Zernike polynomials, which have refractive power values of the third value range class, can for example be fixedly associated with the subgroup. Alternatively, the Zernike polynomials of the first and the second value range class can also be examined for presence of the optimization condition, in particular by which combination the maximized target corneal geometry results.

Particularly preferably, at least one of the value range classes can also be selected, wherein the Zernike polynomials with refractive power values outside of the selected value range class can be fixedly associated with the subgroup. However, the refractive power values within the value range class can be varied by the optimization calculation such that they achieve a maximized target corneal geometry. Hereto, it can be preset that the refractive power values are only allowed to be varied within the refractive power value range preset by the value range class. This means that in a refractive power value range up to 0.25 diopters, wherein this is to be understood as a magnitude value, and the refractive power value range therefore ranges from −0.25 diopters to 0.25 diopters, are allowed to be varied within this range such that the maximized target corneal geometry can finally be found.

After determining the subgroup by the optimization calculation, an optimized tissue removal geometry for the removal of the tissue can be ascertained in a step S18 in that the Zernike polynomials of the subgroup are combined. This tissue removal geometry optimized by the combination of the Zernike polynomials of the subgroup can finally be provided as control data for controlling the eye surgical laser 12 in a step S20. Thus, the desired treatment result can be achieved for a patient on the one hand and a safety can be increased on the other hand since less tissue of the cornea has to be removed and the target corneal geometry can be better adapted to an individual patient cornea, respectively, and thereby a larger residual volume of the cornea remains.

Overall, the examples show how a maximum residual tissue for a cornea after treatment by the treatment apparatus 10 can be achieved by the invention.

What is claimed is:

1. A method for providing control data for an eye surgical laser of a treatment apparatus for the removal of a tissue, wherein the method comprises the following steps performed by a control device:
    ascertaining a wavefront of a cornea of a human or animal eye from predetermined examination data;
    ascertaining Zernike polynomials from the ascertained wavefront, wherein the Zernike polynomials describe imaging errors;
    calculating a respective tissue geometry for each Zernike polynomial, wherein an alteration of the cornea for correcting the imaging errors is specified by the respective tissue geometry and wherein a combination of a selection of the Zernike polynomials describes a tissue removal geometry;
    ascertaining a subgroup of the ascertained Zernike polynomials by an optimization calculation, by which one or more Zernike polynomials are selected for the subgroup if they satisfy a preset optimization condition, wherein the optimization condition is preset by a maximized target corneal geometry and an imaging correction to be achieved, wherein the target corneal geometry is ascertained from a difference of a corneal geometry and the tissue removal geometry;
    ascertaining an optimized tissue removal geometry of the tissue to be removed using the ascertained subgroup of the Zernike polynomials, wherein the optimized tissue removal geometry is determined using a combination of the tissue geometries of the Zernike polynomials of the subgroup; and
    providing the control data for controlling the eye surgical laser, which uses the optimized tissue removal geometry for separating the tissue.

2. The method according to claim 1, wherein a refractive correction to be achieved is preset by the imaging correction of the optimization condition, wherein the Zernike polynomials, which are used to achieve the refractive correction, are fixedly associated with the subgroup, wherein the remaining Zernike polynomials, which are not fixedly associated with the subgroup, are examined for presence of the maximized target corneal geometry of the optimization condition.

3. The method according to claim 2, wherein the Zernike polynomials up to a second order are preset for the refractive correction.

4. The method according to claim 1, wherein an aberration correction to be achieved is preset by the imaging correction of the optimization condition, wherein the Zernike polynomials, which are used to achieve the aberration correction, are fixedly associated with the subgroup, wherein the remaining Zernike polynomials, which are not fixedly associated with the subgroup, are examined for presence of the maximized target corneal geometry of the optimization condition.

5. The method according to claim 4, wherein the Zernike polynomials from a third order are preset for the aberration correction.

6. The method according to claim 1, wherein the optimization condition is preset by a resulting geometry and/or morphology and/or thickness of the target corneal geometry.

7. The method according to claim 1, wherein the optimization condition is satisfied if a thickness or a volume of the target corneal geometry is maximized.

8. The method according to claim 1, wherein the Zernike polynomials are associated with the subgroup with a factor determined by the optimization calculation, wherein a value between 0 and 1 is calculated for the factor.

9. The method according to claim 1, wherein a refractive power value, in particular a dioptric equivalent value, is determined for respective ranges of the respective Zernike polynomials, wherein an association of the one or more Zernike polynomials with the subgroup is performed depending on at least one preset refractive power value range.

10. The method according to claim 9, wherein a refractive power value range is preset for each Zernike polynomial and/or for each order of the Zernike polynomials.

11. The method according to claim 9, wherein one or more value range classes with respective refractive power value ranges are preset, wherein the respective ranges of the respective Zernike polynomials are classified into the preset value range classes depending on the refractive power value, wherein it is classified by the value range classes how important the respective range is for the imaging correction to be achieved, wherein the association of the one or more Zernike polynomials with the subgroup is performed depending on the value range classes.

12. The method according to claim 11, wherein at least one of the value range classes is selected, wherein the Zernike polynomials with refractive power values outside of the selected value range class are fixedly associated with the subgroup, wherein those refractive power values, which are within the refractive power value range of the selected value range class, are additionally optimized within the refractive power value ranges of the selected value range classes for maximizing the target corneal geometry by the optimization calculation.

13. The method according to claim 11, wherein at least one of the value range classes is selected, wherein the refractive power values of all of the value range classes are optimized for maximizing the target corneal geometry by the optimization calculation, wherein the refractive power values are increased or reduced by a respective optimization value for optimization, wherein the respective optimization value is within the refractive power value ranges of the selected value range classes.

14. The method according to claim 11, wherein the ranges of the Zernike polynomials are divided into three value range classes, wherein a first value range class includes refractive power values below 0.25 diopters and is categorized as clinically non-relevant, a second value range class includes refractive power values between 0.25 diopters and 0.5 diopters and is categorized as possibly clinically relevant and a third value range class comprises refractive power values above 0.5 diopters and is categorized as clinically relevant, wherein Zernike polynomials, which have the third value range class or have a combination of the second and the third value range class, are fixedly associated with the subgroup, wherein the remaining Zernike polynomials, which are not fixedly associated with the subgroup, are examined for presence of the maximized target corneal geometry of the optimization condition.

15. A control device, which is formed to perform a method according to claim 1.

16. A treatment apparatus with at least one eye surgical laser for the removal of a tissue of a human or animal eye, in particular of a lenticule, using photodisruption and/or photoablation, and at least one control device according to claim 15.

17. The treatment apparatus according to claim 16, wherein the at least one eye surgical laser is formed to emit laser pulses in a wavelength range between 300 nm and 1400 nm at a respective pulse duration between 1 fs and 1 ns, and a repetition frequency of greater than 10 kHz.

18. The treatment apparatus according to claim 16, wherein the control device comprises at least one storage device for at least temporary storage of at least one control dataset, wherein the control dataset or datasets include(s) control data for positioning and/or focusing individual laser pulses in the cornea; and includes at least one beam device for beam guidance and/or beam shaping and/or beam deflection and/or beam focusing of a laser beam of the at least one eye surgical laser.

19. A computer program including commands, which cause a treatment apparatus with at least one eye surgical laser for the removal of a tissue of a human or animal eye, in particular of a lenticule, by means of using photodisruption and/or photoablation, and at least one control device to execute a method according to claim 1.

20. A non-transitory computer-readable medium, on which the computer program according to claim 19 is stored.

* * * * *